United States Patent
Boone et al.

(10) Patent No.: US 11,540,789 B1
(45) Date of Patent: Jan. 3, 2023

(54) SELF-SHIELDED X-RAY COMPUTED TOMOGRAPHY SYSTEM

(71) Applicants: Izotropic Corporation, Surrey (CA); The Regents of the University of California, Oakland, CA (US)

(72) Inventors: John M. Boone, Oakland, CA (US); John McGraw, Surrey (CA); Andrew M. Hernandez, Oakland, CA (US); Younes Achkire, Surrey (CA)

(73) Assignees: Izotropic Corporation, Surrey (CA); The Resents of the University of California, Oakland, CA (US)

( * ) Notice: Subject to any disclaimer, the term of this patent is extended or adjusted under 35 U.S.C. 154(b) by 0 days.

(21) Appl. No.: 17/727,540

(22) Filed: Apr. 22, 2022

(51) Int. Cl.
*A61B 6/00* (2006.01)
*A61B 6/04* (2006.01)
*A61B 6/10* (2006.01)
*A61B 6/03* (2006.01)

(52) U.S. Cl.
CPC ............ *A61B 6/0435* (2013.01); *A61B 6/035* (2013.01); *A61B 6/107* (2013.01); *A61B 6/4085* (2013.01); *A61B 6/4435* (2013.01); *A61B 6/502* (2013.01)

(58) Field of Classification Search
CPC .......... A61B 6/502; A61B 6/032; A61B 6/107
See application file for complete search history.

(56) References Cited

U.S. PATENT DOCUMENTS

| | | | |
|---|---|---|---|
| 7,679,073 B2 | 3/2010 | Urano et al. |
| 7,817,774 B2 | 10/2010 | Partain et al. |
| 7,905,660 B2 | 3/2011 | Sukovic et al. |
| 8,842,806 B2 | 9/2014 | Packard et al. |
| 9,968,308 B2 | 5/2018 | Kawase et al. |
| 10,064,592 B2 | 9/2018 | Kawase et al. |
| 10,098,600 B2 | 10/2018 | Ning et al. |
| 10,231,683 B2 | 3/2019 | Shimada et al. |

(Continued)

FOREIGN PATENT DOCUMENTS

WO 2021-158558 A1 8/2021

OTHER PUBLICATIONS

PCT/EP2022/26551 Written Opinion dated Aug. 18, 2022.
PCT/EP2022/26551 International Search Report dated Aug. 18, 2022.

*Primary Examiner* — Dani Fox
(74) *Attorney, Agent, or Firm* — Venable LLP; Henry J. Daley; Aziz H. Poonawalla

(57) ABSTRACT

A system for breast computed tomography includes a table supporting a patient in a prone position with an opening positioned for a breast of the patient to extend downwards therethrough, a gantry assembly positioned beneath the table with a platform driven to rotate by a motor, an x-ray source assembly coupled to the platform to rotate therewith and positioned to irradiate with an x-ray beam at least a portion of the breast, and a detector assembly coupled to the platform to rotate therewith and positioned to receive the x-ray beam from the x-ray source assembly. The system includes a shielding enclosure rigidly mounted atop the platform to rotate therewith, enclosing during rotation of the platform the detector assembly, the breast, and the x-ray beam, and having walls composed of a material and a thickness to attenuate an x-ray beam of a predetermined energy and intensity by a predetermined amount.

23 Claims, 14 Drawing Sheets

(56) References Cited

U.S. PATENT DOCUMENTS

| | | |
|---|---|---|
| 10,383,587 B2 | 8/2019 | Tsujii et al. |
| 10,531,844 B1 * | 1/2020 | Ghazi ................. A61B 6/4435 |
| 10,660,587 B2 | 5/2020 | Choy et al. |
| 2007/0030958 A1 | 2/2007 | Munger |
| 2007/0112854 A1 | 5/2007 | Franca |
| 2010/0133450 A1 | 6/2010 | Belson |
| 2012/0187310 A1 | 7/2012 | Neushul |
| 2013/0108016 A1 | 5/2013 | Tonami |
| 2014/0336502 A1 | 11/2014 | Neelakanta et al. |
| 2015/0173690 A1 | 6/2015 | Ning et al. |
| 2017/0332988 A1 | 11/2017 | Tsujii et al. |
| 2018/0064408 A1 | 3/2018 | Shimada et al. |
| 2020/0146640 A1 | 5/2020 | Achkire et al. |
| 2020/0305820 A1 | 10/2020 | Barbabella et al. |
| 2021/0113168 A1 | 4/2021 | Smith et al. |
| 2021/0219933 A1 * | 7/2021 | Boone ................. A61B 6/0421 |

* cited by examiner

SELF-SHIELDED X-RAY COMPUTED TOMOGRAPHY SYSTEM

BACKGROUND

1. Technical Field

Currently claimed embodiments of the invention relate to systems and components for breast examinations and procedures, and more particularly to systems that have an x-ray shield enclosure, to the x-ray shield enclosure, and to methods of production.

2. Discussion of Related Art

While the current state-of-the-art for breast imaging is typically digital mammography, sometimes coupled with limited angle tomography which is often called breast tomosynthesis, it is recognized by the breast imaging community that these two-dimensional or pseudo-three-dimensional imaging modalities do not fully address the needs of breast cancer detection, diagnosis, and evaluation. Several groups have studied the use of computed tomography principles for breast imaging. These studies generally describe imaging a single breast at a time with the patient laying prone on a table, with the patient's breast hanging through a hole in the table in so-called pendant position.

However, such breast computed tomography (CT) based systems pose a safety risk to radiation workers and others, due to the geometry of the x-ray source as it rotates around the pendant breast. Mitigation of this exposure risk requires specially constructed x-ray screening rooms with heavy and expensive shielding on all four walls, floor, and ceiling. The resulting footprint of the breast CT system is therefore not limited to the footprint system itself, but rather a much larger restricted area with constraints on nearby foot traffic within the facility. Solutions for shielding of the breast CT system are desired that would make additional room shielding and/or a large, restricted area unnecessary, to reduce cost without sacrificing safety.

SUMMARY

According to an embodiment of the invention, a system for breast examinations and procedures includes a table configured to support a patient in a prone position, the table defining an opening that is positioned for a breast of the patient to extend downwards therethrough. The system also includes a gantry assembly positioned beneath the table, said gantry assembly comprising a platform and a drive assembly configured to rotate said platform relative to said table. The system also includes an x-ray shield enclosure attached to said platform of said gantry so as to be rotatable along with said platform, said x-ray shield enclosure defining a substantially enclosed space therein and further defining an opening through a side thereof that is aligned with said opening defined by said table for said breast of said patient to extend downwards therethrough at least partially into said space defined by said x-ray shield enclosure. The system also includes an x-ray assembly attached to the x-ray shield enclosure so as to be rotatable therewith, said x-ray assembly comprising an x-ray source positioned to irradiate with an x-ray beam at least a portion of the breast during operation. The system also includes a detector assembly attached to the x-ray shield enclosure to be rotatable therewith, the detector assembly comprising an x-ray detector positioned to receive at least a portion of the x-ray beam after passing through the breast, wherein the x-ray shield enclosure attenuates x-rays from said x-ray source sufficiently for users of said system to be in a vicinity of said x-ray shield enclosure during operation of said system without further shielding while complying with radiation safety.

According to another embodiment of the invention, an x-ray shield enclosure for a system for breast examinations and procedures includes x-ray attenuating material forming a substantially enclosing box defining a substantially enclosed space therein, wherein a side of said substantially enclosing box defines an opening therethrough that is suitable to be aligned with an opening defined by a table of said system such that a breast of a patient can extend downwards through said opening of said x-ray shield enclosure at least partially into said space defined by said x-ray shield enclosure, wherein said x-ray shield enclosure is further configured to be attached to a rotatable platform of a gantry of said system so as to be rotatable along with said platform, and wherein the x-ray shield enclosure attenuates x-rays from an x-ray source sufficiently for users of said system to be in a vicinity of said x-ray shield enclosure during operation of said system without further shielding while complying with radiation safety.

According to another embodiment of the invention, a method of manufacturing a system for breast examinations and procedures includes providing a table configured to support a patient in a prone position, the table defining an opening that is positioned for a breast of the patient to extend downwards therethrough. The method also includes providing a gantry assembly positioned beneath the table, said gantry assembly comprising a platform and a drive assembly configured to rotate said platform relative to said table. The method also includes attaching an x-ray shield enclosure to said platform of said gantry so as to be rotatable along with said platform, said x-ray shield enclosure defining a substantially enclosed space therein and further defining an opening through a side thereof that is aligned with said opening defined by said table for said breast of said patient to extend downwards therethrough at least partially into said space defined by said x-ray shield enclosure. The method also includes attaching an x-ray assembly to the x-ray shield enclosure so as to be rotatable therewith, said x-ray assembly comprising an x-ray source positioned to irradiate with an x-ray beam at least a portion of the breast during operation. The method also includes attaching a detector assembly to the x-ray shield enclosure to be rotatable therewith, the detector assembly comprising an x-ray detector positioned to receive at least a portion of the x-ray beam after passing through the breast, wherein the x-ray shield enclosure attenuates x-rays from said x-ray source sufficiently for users of said system to be in a vicinity of said x-ray shield enclosure during operation of said system without further shielding while complying with radiation safety.

According to another embodiment of the invention, a method of producing an x-ray shield enclosure for a system for breast examinations and procedures includes forming a substantially enclosing box from x-ray attenuating material so as to define a substantially enclosed space therein, and forming an opening through a side of said substantially polygonal box, said opening being suitable to be aligned with an opening defined by a table of said system such that a breast of a patient can extend downwards through said opening of said x-ray shield enclosure at least partially into said space defined by said x-ray shield enclosure, wherein said x-ray shield enclosure is further configured to be attached to a rotatable platform of a gantry of said system so as to be rotatable along with said platform, and wherein the x-ray shield enclosure attenuates x-rays from an x-ray source sufficiently for users of said system to be in a vicinity of said x-ray shield enclosure during operation of said system without further shielding while complying with radiation safety.

BRIEF DESCRIPTION OF THE DRAWINGS

Further objectives and advantages will become apparent from a consideration of the description, drawings, and examples.

DETAILED DESCRIPTION

Figure 1:
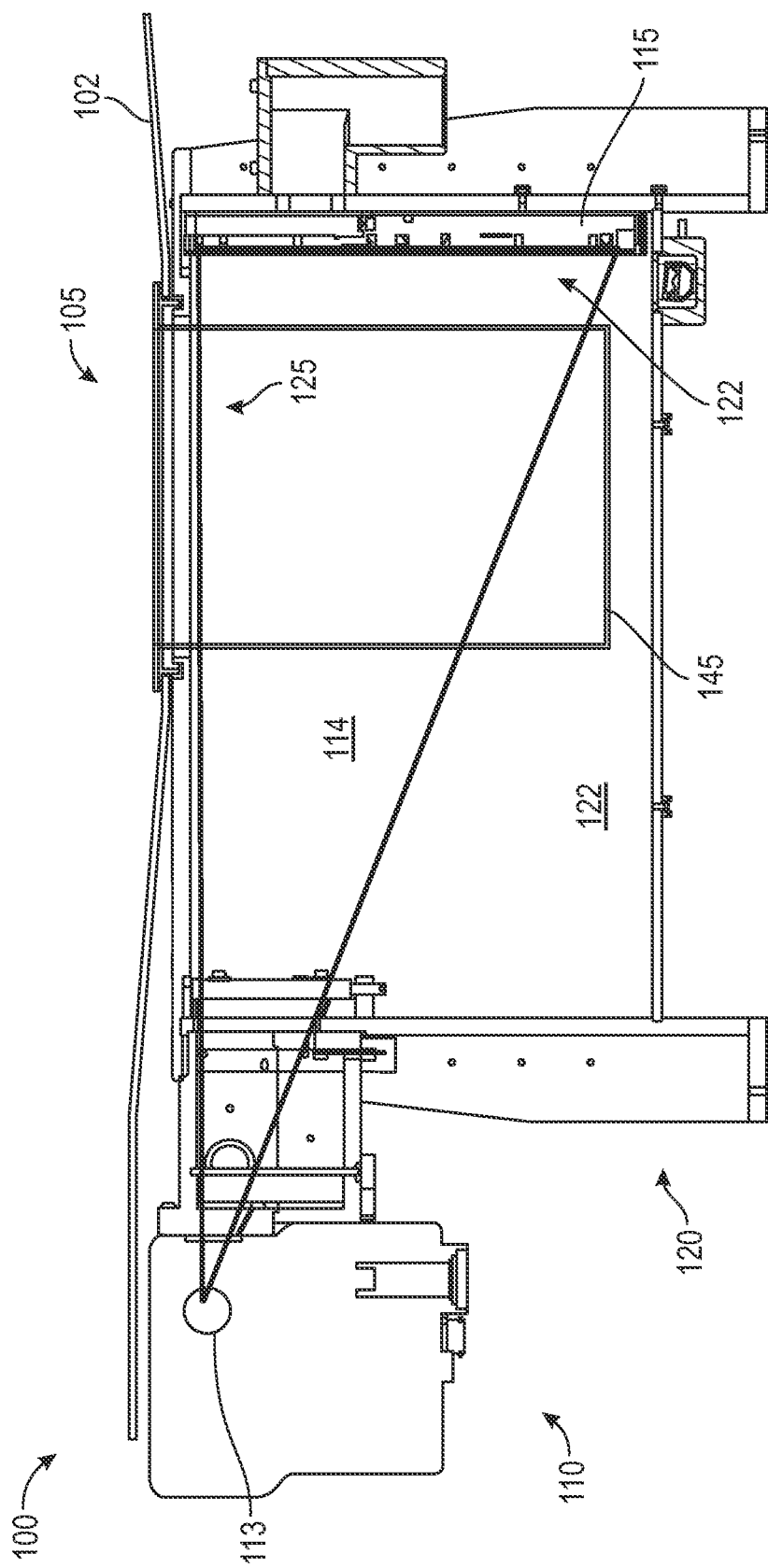
FIG. 1 shows a cross-sectional view of a self-shielded CT system according to some embodiments of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed, and other methods developed, without departing from the broad concepts of the current invention. All references cited anywhere in this specification, including the Background and Detailed Description sections, are incorporated by reference as if each had been individually incorporated.

Some embodiments of the current invention describe systems and methods for radiation protection to reduce the radiation risk to workers and users of systems. Such radiation risks can be by proximity directly around the system without additional shielding, or due to exposure in poorly-designed or poorly-constructed X-ray imaging diagnostics or screening rooms. An embodiment of the current invention includes a self-shielded X-ray imaging subsystem that substantially fully encloses an x-ray source and detector of a computed tomography (CT) system into an x-ray shield enclosure. The term "CT system" as used herein is intended to have a broad meaning to include, for example, but not limited to, a full CT system that scans a full 360° (or 180°), a cone beam CT system, or a fan beam CT system.

An advantage of a self-shielded x-ray imaging system, according to some embodiments, is that it can obviate the need for additional room shielding, or the need for large restricted areas. The x-ray shield enclosure can be made from one or more optically dense metals such as lead, tungsten, steel, etc. or combinations thereof so as to reduce the intensity of any x-rays that pass through the material. The term "optically dense" is intended to mean that the material attenuates a substantial portion of the x-rays incident thereon. The general concepts of the current invention are not limited to only these examples of materials. Generally, high-Z materials that have larger numbers of protons in the nucleus of the atomic element, i.e., atomic number "Z", attenuate x-rays to a greater extent. The term "high-Z material" is intended to be any material with an atomic number Z greater than or equal to 21.

The amount of attenuation of the x-rays is also related to the thickness of the material used. In general, the greater the thickness, the greater the attenuation of the x-rays. For a high degree of attenuation, one can also think of the material as "blocking" the x-rays from passing entirely through the material. The wall thicknesses can be selected such that the system produces radiation leakage exposure levels (i.e., outside the medical device) that are safe to the public while operating under a full clinical workload. In some embodiments. the shielding calculation can take into account the x-ray radiation of two types: a collimated x-ray beam from the x-ray source, and the scattered x-ray radiation from the patient body part that is being imaged. The occupational radiation limit may be stipulated by the Nuclear Regulatory Commission (NRC) or agreement institutions.

Some embodiments of the current invention are directed to a self-shielded x-ray CT system for at least one of breast examinations and procedures, with shielding that fully encloses the x-ray source and detector of the CT system into an enclosure.

The term "breast examinations" is intended to include but is not limited to x-ray imaging of the breast. The x-ray imaging can include, but is not limited to, cone-beam x-ray imaging, x-ray computed tomography, and mammography, for example. The term "breast procedures" can include but is not limited to surgery (for example, image-guided surgery and radiosurgery), biopsy (e.g., image-guided biopsy), and therapy (for example, radiation therapy).

The term "fully enclose" can include cases in which at least the aperture portion of the x-ray source is fully enclosed in some embodiments. The shielded enclosure material (i.e. dense metals such as lead, tungsten, steel, etc.) and wall thicknesses are selected such that radiation leakage exposure levels (i.e., outside the enclosure) are safe to the public while operating under a full clinical workload. The materials and thicknesses are selected to take into account the primary radiation emitted from the x-ray beam, as well as secondary radiation scattered from the patient body part (e.g., the breast) to be scanned. In some embodiments, the design follows occupational radiation limits stipulated by the Nuclear Regulatory Commission (NRC) or agreement institutions.

For example, in some embodiments of the current invention the system is designed according to the regulations specified in the National Council on Radiation Protection (NCRP) (See: National Council on Radiation Protection and Measurements (2004) Structural Shielding Design for Medical X-ray Imaging Facilities. Bethesda: NCRP; NCRP Report 147, incorporated herein by reference), to provide a maximum dose of 18 mGy to the breast, while providing radiation protection sufficient to maintain a safety level of under 0.02 mGy per week to non-controlled areas, and 0.1 mGy to controlled areas. These safety design goals assume a worst-case scenario of an occupancy factor of one (the fraction of time occupied by a person who spends the most time near the device), a use factor of one (the fraction of the primary beam workload that is directed towards a given barrier), a maximum of 160 patients per forty-hour work week (i.e., one patient every fifteen minutes), and five scans per patient (bilateral scans, each with and without contrast, and one extra scan). These limits also assume that, with 0.2 mm Cu filtration, the air kerma at the isocenter to deliver the target dose is nominally 16.46 mGy and is a maximum of 23.48 mGy, assuming 12 mGy dose for 60 kV nominal exposure and 18 mGy dose for 70 kV maximum exposure. In other embodiments, the safety design goals may be higher or lower, depending on different values for occupancy and use factors, patient load, scans per patient, and/or characteristics of the x-ray tube.

FIG. 1 shows a cross-sectional view of a system 100 for breast examinations and procedures according to some embodiments of the current invention. In these embodiments, the system 100 is a self-shielded CT system. The system 100 includes a table 102 that is configured to support a patient in a prone position. The table 102 defines an opening 105 that is positioned for a breast of the patient to extend downwards therethrough. In this embodiment, there is a single opening 105 for one breast. The table 102 can have dimensions and a surface shape to allow the patient to position either breast through the opening 105, or each one in sequence. The general concepts of the current invention are not limited to a single opening through the table; however, one opening 105 has been found to be suitable according to some embodiments.

The system 100 also includes an x-ray assembly 110 and a detector assembly 112. The x-ray assembly 110 has at least one x-ray source 113 (e.g., one or more x-ray tubes, each x-ray tube with one or more focal spots) that generates an x-ray beam 114. The term "x-ray source" is intended to refer to an x-ray apparatus (e.g., an x-ray tube) that generates x-ray beams at a specific range of energies. In some embodiments, the range of energies and intensities may be appropriate for x-ray imaging. In other embodiments, the range of energies and intensities may include but is not limited to energy ranges for one or more of x-ray surgery, radiation therapy, or other examinations or procedures.

The x-ray assembly 110 is positioned to irradiate, with the generated x-ray beam 114, at least a portion of the breast during operation. The detector assembly 112 has an x-ray detector 115 (e.g., a flat-panel detector in some embodiments) that is positioned to receive at least a portion of the x-ray beam 114 after the x-ray beam 114 passes through the breast.

The system 100 also includes an x-ray shield enclosure 120 that is attached to the x-ray assembly 110 and the detector assembly 112. The x-ray shield enclosure 120 defines a substantially enclosed space 122. The x-ray shield enclosure 120 also has an aperture 125 that is aligned with the opening 105 to permit a breast of the patient to extend downwards into the enclosed space 122 defined by the x-ray shield enclosure 120.

The position of the x-ray source 113 and the x-ray detector 115 define a field of view (FOV) for the x-ray beam 114 within the enclosed space 122, and this FOV of the x-ray beam 114 is fully enclosed within the x-ray shield enclosure 120. In some embodiments, the x-ray detector 115 is a flat-panel detector, the x-ray beam 114 is a cone beam, and the system 100 is configured to perform cone-beam computed tomography. However, these are merely examples of x-ray sources and x-ray detectors that can be used in some embodiments, and the general concepts of the current invention are not limited to only this system configuration.

The term "substantially enclosed space" is intended to recognize that x-rays can exit the enclosed space 122 through the patient's breast into and possibly through the women's body. A radiation shielding blanket, for example, could be placed on the women's back to reduce radiation that could emerge in that way. This term also recognizes that the substantially enclosed space 122 will be defined after the x-ray shield enclosure 120 is fully assembled, additional system elements (e.g., an x-ray assembly 110, a detector assembly 112, etc.) are attached over corresponding ports, and any access doors are closed.

The x-ray shield enclosure 120 attenuates x-rays from the x-ray source (including the x-ray beam 114, as well as scattered radiation off of the breast, the detector, and the inside surfaces of the x-ray shield enclosure 120 itself), sufficiently for users of the system 100 to be in a vicinity of the x-ray shield enclosure 120 during operation of the system 100, without requiring further shielding, and while still complying with radiation safety requirements.

In some embodiments, the system 100 also includes a safety shield 145 that is rigidly mounted to and under the table 102, so that the safety shield 145 remains static during rotation of the platform and the x-ray shield enclosure 120. The safety shield 145 physically protects the patient's breast during operation of the system 100, and maintains a separate, clean environment that is isolated from the mechanical and moving components of the system 100 inside the enclosed space 122. In order to avoid interference with the imaging process, the safety shield 145 is substantially transparent to the x-ray beam and light, for example being made of transparent plastic according to some embodiments. However, this is merely an example of a material that can be used for the plastic shield in some embodiments, and the general concepts of the current invention are not limited to only this embodiment.

Figure 2A:
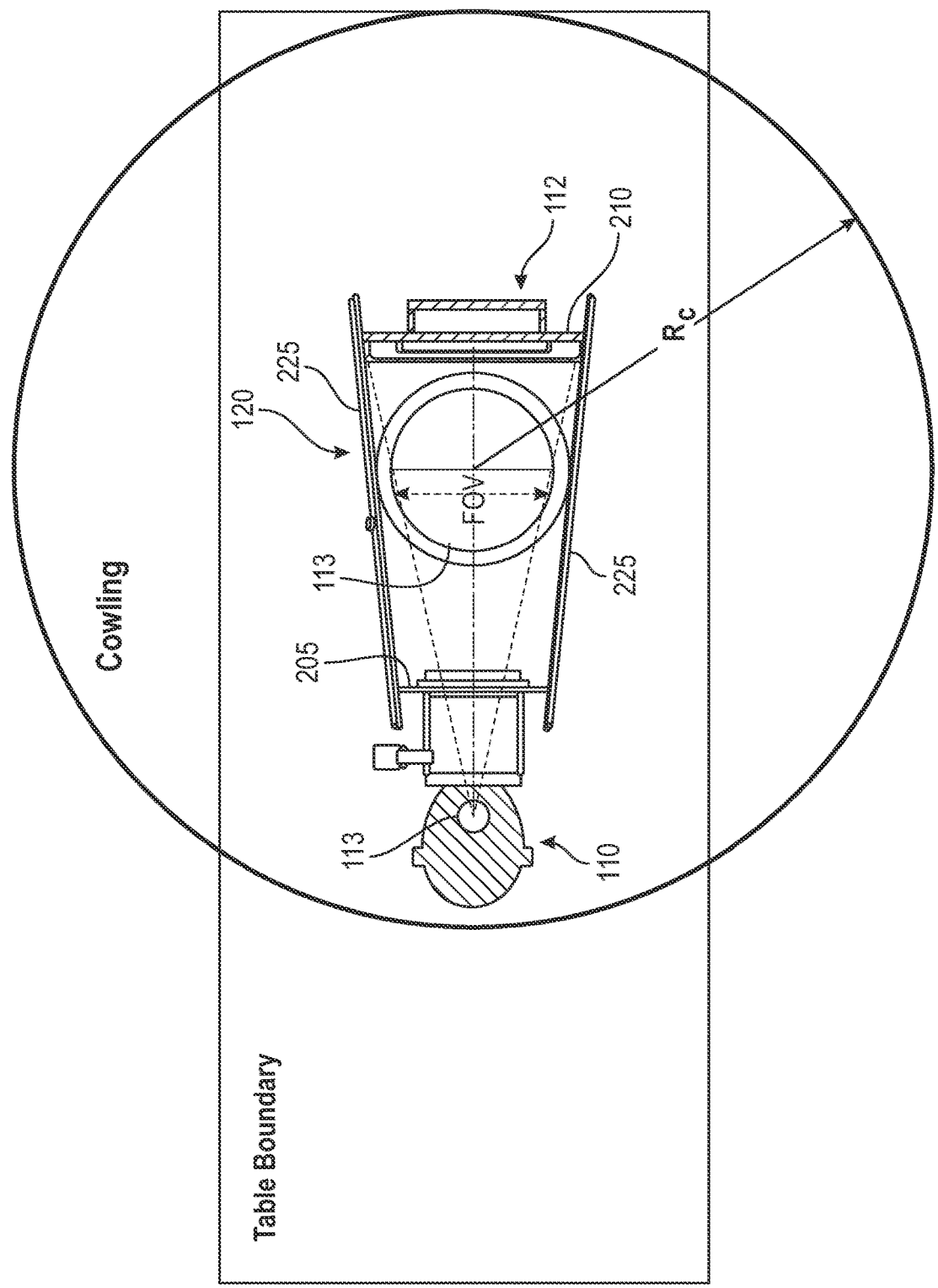
FIG. 2A and FIG. 2B show schematic diagrams of top and side views, respectively, of the shield enclosure shown in FIG. 1.
Figure 2B:
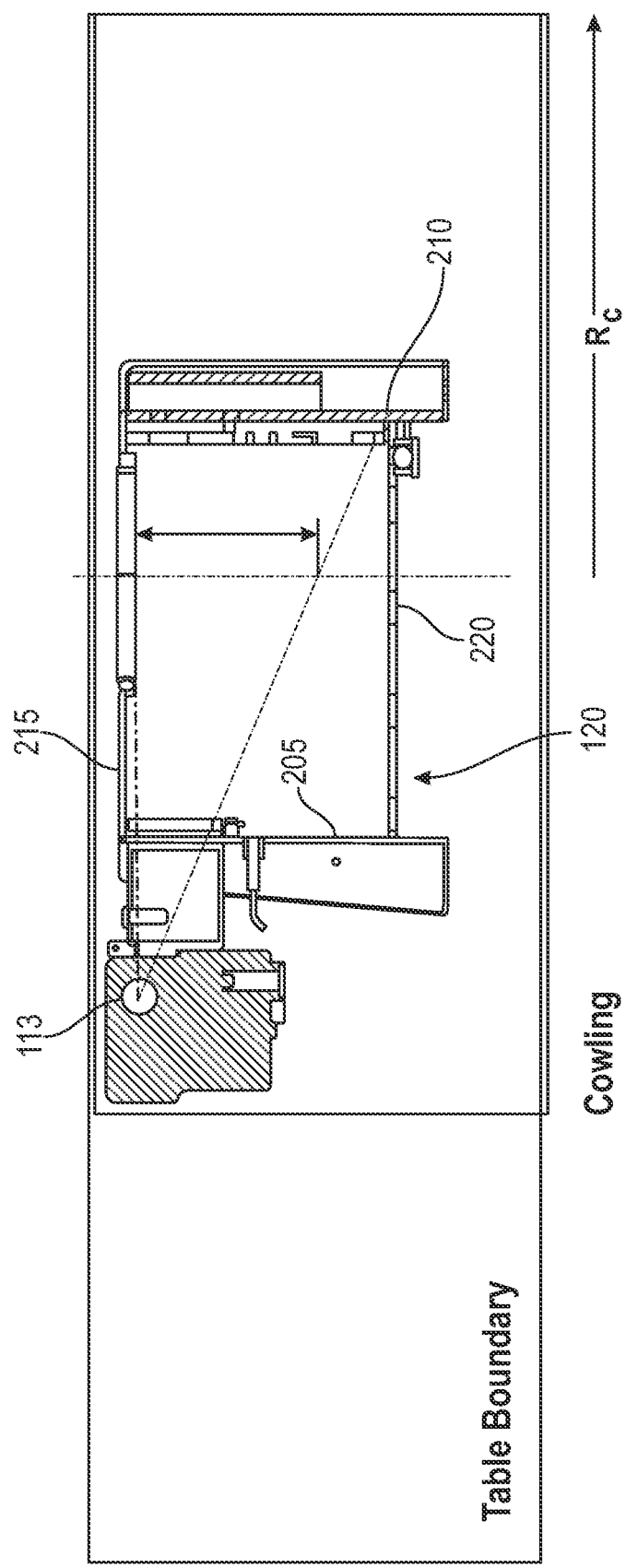

FIG. 2A and FIG. 2B show schematic diagrams of top and side views, respectively, of the x-ray shield enclosure 120 of some embodiments. In some embodiments, the x-ray shield enclosure 120 is constructed of at least one of steel (e.g., low-carbon steel), lead, tungsten, or other material or alloy with a high atomic number Z. These are merely some examples of materials that can be used in some embodiments, and the general concepts of the invention are not limited to only this embodiment.

The x-ray shield enclosure 120 also has different thicknesses of the panels in some embodiments. The x-ray shield enclosure 120 may have some or all of a back panel 205 to which the x-ray assembly 110 is mounted, a front panel 210 to which the detector assembly 112 is mounted, a top panel 215 with aperture 125, a bottom panel 220, and one or more side panels 225 perpendicular to the back panel 205 and the front panel 210. For example, the x-ray shield enclosure 120 may be have a back wall thickness $X_B$ for the back panel 205, and a thickness XP for the front panel 210. The front panel 210 may also be referred to as the beamstop, since it is directly in the path of the x-ray beam 114. In addition, the x-ray shield enclosure 120 may have a top wall thickness XT for the top panel 215 below the table 102, and a bottom wall thickness $X_{BT}$ for the bottom panel 220. The x-ray shield enclosure 120 may also have side thicknesses $X_S$ for the side panels. In some embodiments, the thicknesses are defined to safely attenuate the x-ray beam 114 and secondary scatter radiation, up to a radius $R_C$ of a physical cowling that is large enough to fully enclose the rotation of a platform 310 (FIG. 3) upon which the x-ray shield enclosure 120 is mounted. The radius $R_C$ is therefore the minimum safety radius that a person may approach to the system 100. Table 1 illustrates an example of values for thicknesses of the panels for an embodiment of the x-ray shield enclosure 120. These are merely some examples of panel configurations and panel thicknesses that can be used in some embodiments, and the general concepts of the invention are not limited to only this embodiment.

TABLE 1

| | Max (mm) | Nominal (mm) | Safety | Design (mm) |
|---|---|---|---|---|
| Primary $X_P$ | 11.057 | 5.537 | 1.997 | 12.700 |
| Secondary Side (door): $X_S$ | 4.256 | 1.907 | 2.232 | 4.763 |
| Secondary side (wall): $X_S$ | — | — | — | 6.350 |
| Secondary Back: $X_B$ | 6.038 | 2.862 | 2.110 | 12.700 |
| Secondary Top: $X_T$ | 2.839 | 1.186 | 2.393 | 12.700 |
| Secondary Bottom ($X_{BT}$) | −9.752 | −11.460 | — | 6.350 |

The dimensions of the x-ray shield enclosure 120 and the positions of the x-ray assembly 110 and the detector assembly 112 are selected in some embodiments to minimize blur, which is the penumbra of the x-ray beam 114 due to the focal spot size of the x-ray source 113, while maintaining an acceptable access around the patient's breast. The size of the aperture may be selected to maximize chest wall coverage, while minimizing the magnification factor of the image.

Figure 3A:
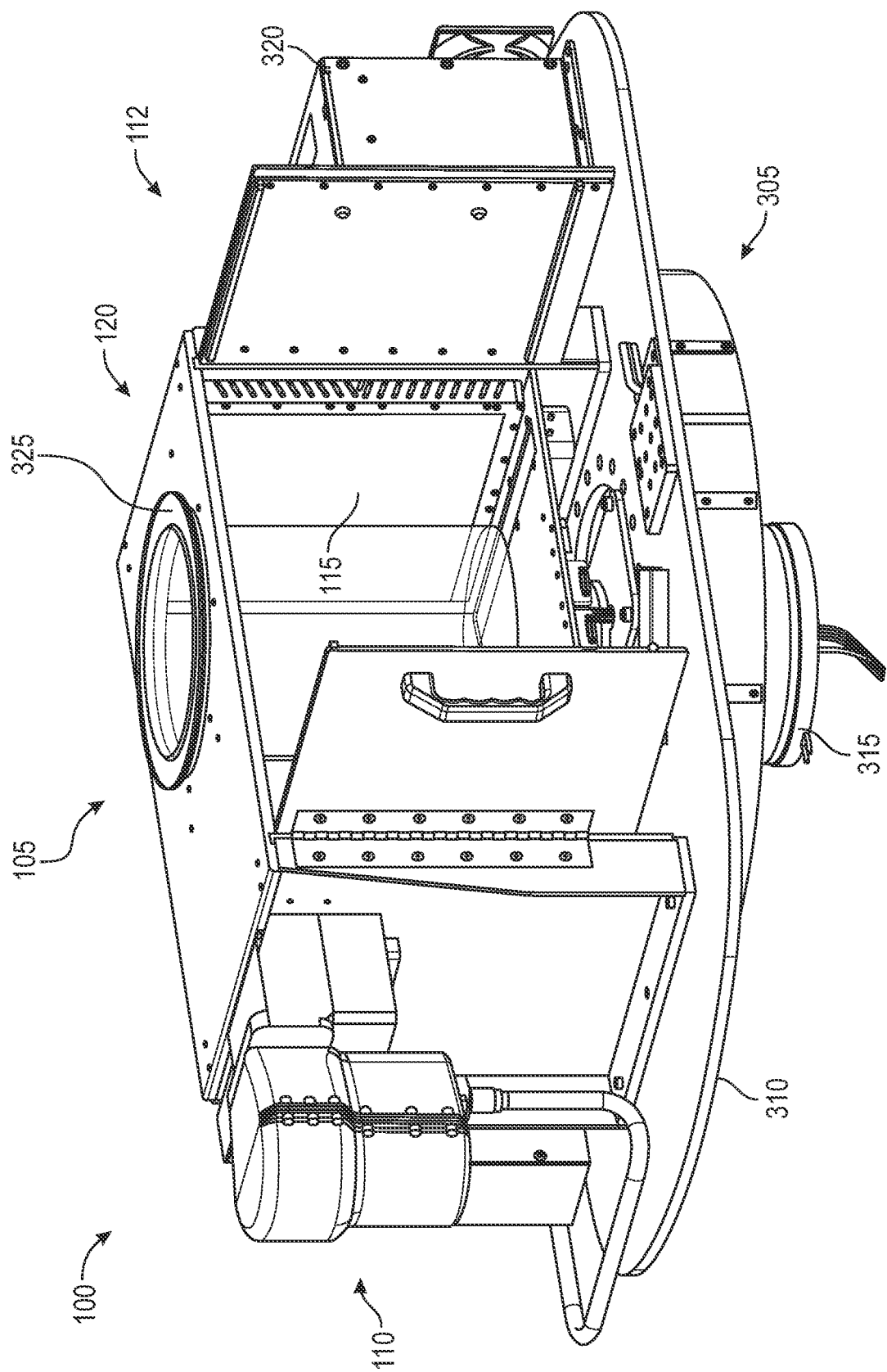
FIG. 3A shows a perspective view of the self-shielded CT system of FIG. 1.

FIG. 3A shows a perspective view of the system 100 of FIG. 1. As can be seen in this view, the system 100 also includes a gantry assembly 305 positioned beneath the table 102 (omitted from FIG. 3). The gantry assembly 305 includes a platform 310 and a drive assembly 315 configured to rotate the platform 310 relative to the table 102. For example, in some embodiments the gantry rotation speed is 6 revolutions per minute (RPM) or more, so that each scan of the patient breast is 10 seconds or less, to allow the patient to hold their breath during the scan.

In some embodiments, the x-ray shield enclosure 120 is directly mounted to the platform 310, so that the x-ray shield enclosure 120 rotates along with the platform 310, while the table 102 stays stationary. Since the x-ray assembly 110 and the detector assembly 112 are directly mounted to the x-ray shield enclosure 120, they also rotate with the platform 310 and the x-ray shield enclosure 120 relative to the table 102. The platform 310 also supports additional electronic components of the x-ray assembly 110 and the detector assembly 112, including but not limited to a kilovolt (kV) generator 320 that feeds the x-ray source 113. In some embodiments, the kV generator 320 provides 70 kV, 12 kW, and a 4 ms pulse.

Figure 3B:
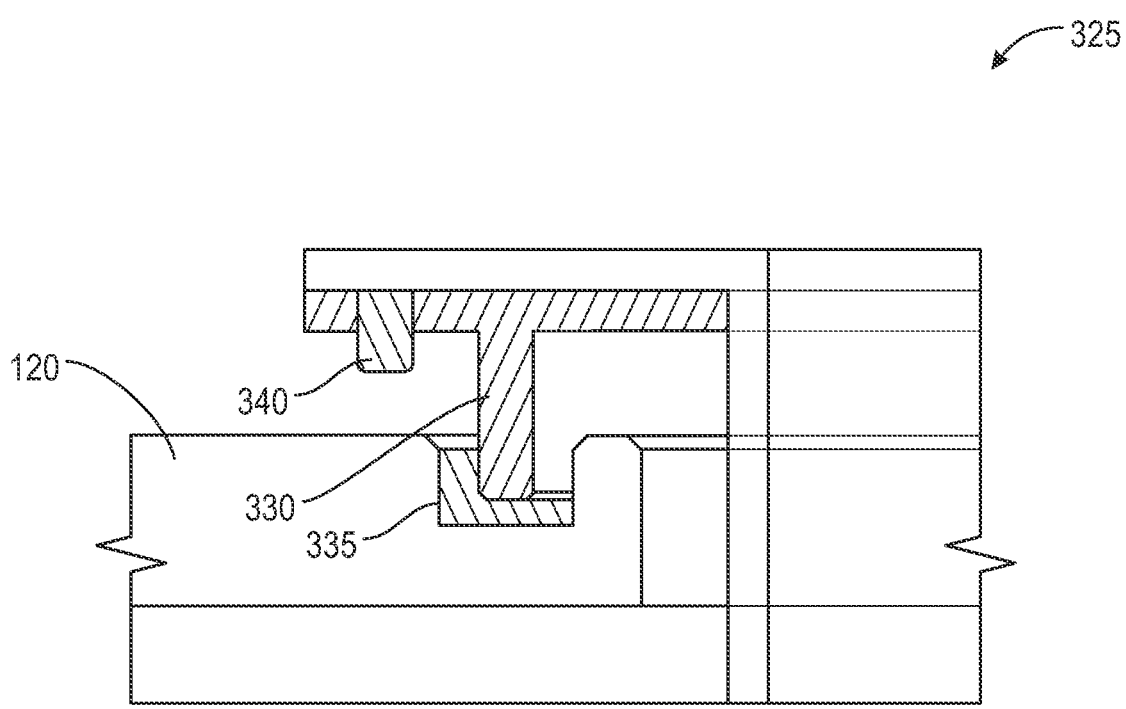
FIG. 3B shows a ring interface that is attached to the patient table, that allows relative rotation between the shield enclosure and the patient table.

In some embodiments, as shown in FIG. 3B, the system 100 also includes a ring interface 325 that is attached to the table 102, that allows relative rotation between the x-ray shield enclosure 120 and the table 102. The ring interface 325 allows the x-ray shield enclosure 120 to rotate freely during rotation of the platform 310 (not shown in FIG. 3B), while preventing stray radiation (i.e., unattenuated x-rays) from leaking out from the enclosed space 122. In the example of FIG. 3B, the radiation leakage is prevented using a tongue and groove design, in which the ring interface 325 has a tongue 330 which fits into a groove 335 in the table-facing surface of the x-ray shield enclosure 120. In this example, there is a 3 mm clearance between the tongue 330 and the groove 335, to ensure unobstructed rotation, while creating a tortuous pathway that prevents stray radiation from the enclosed space 122 from exiting through the opening 105 in the table and the aperture 125 in the x-ray shield enclosure 120. In some embodiments, the ring interface 325 is aligned to maintain the clearance between the tongue 330 and the groove 335, by using a dowel pin 340, which ensures that the opening 105 and the aperture 125 are aligned to each other and with a rotation axis of the gantry assembly 305.

Figure 3C:
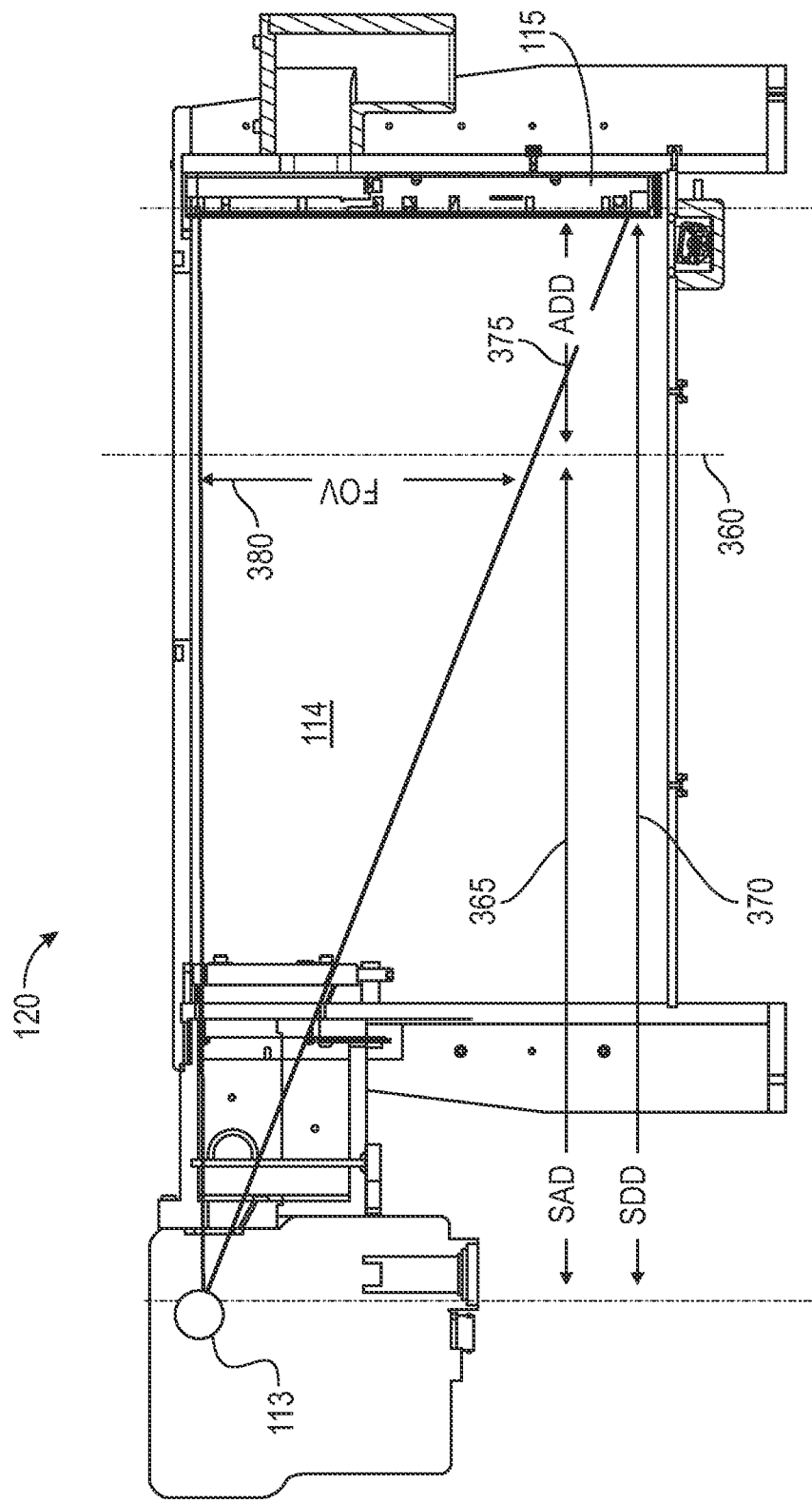
FIG. 3C shows the relationships of the dimensions of the shield enclosure to the magnification factor.

FIG. 3C shows the relationships of the dimensions of the x-ray shield enclosure 120 to the magnification factor. The distance of the x-ray source 113 to the gantry axis 360 is defined as the source-axis distance (SAD) 365, and the distance of the x-ray source 113 to the x-ray source 113 to the x-ray detector 115 is defined as the source-detector distance (SDD) 370. The difference between the SAD 365 and the SDD 370 is defined as the axis-detector distance (ADD) 375. In some embodiments, the SAD 365 constrains the radius of the gantry assembly 305. For example, in some embodiments, the gantry radius is constrained to be no larger than 800 mm, to ensure that the system 100 can fit in a standard mammography room of 3 meters by 4 meters. If the ADD 375 is chosen to be 175 mm, then the maximum SDD 370 would be 775 mm (to allow for an 800 mm maximum gantry radius). The resulting SAD is therefore 600 mm, resulting in a magnification factor M of SDD/SAD that is equal to 1.29. For example, for an x-ray detector 115 that provides 3052 pixels×3052 pixel resolution, 0.1 mm pixel pitch, the active area would 305.2 mm, which results in a field of view (FOV) 380 of 236 mm. In other embodiments, the magnification may be higher or lower, depending on different values for system size requirements and/or characteristics of the x-ray detector.

The term "x-ray shield enclosure" is intended to have a broad meaning to include any suitable shape. For example, the x-ray shield enclosure 120 can be in the form of a polygonal box, such as, but not limited to, a square or rectangular box, with multiple panels to enclose the space 122 on the top, bottom, and sides. The x-ray shield enclosure 120 could also be in the form of a cylindrical, or flattened cylindrical shape, for example, with enclosing circular or oval tops and bottoms. These are only examples and do not limited the general concepts of this invention.

The panels of the x-ray shield enclosure 120 may be straight or curved, as needed to define the overall shape. Two adjacent sides of the x-ray shield enclosure 120 may be formed of two separate panels that have been joined, or may be separated by a bend in an integral sheet of material. In such cases where two separate panels have been joined, a seam exists between the panels, which is constructed so as to minimize x-ray leakage along the seam. The adjacent panels may be joined by mating interfaces (e.g., tongue-and-groove interfaces), that have been welded together using stitch welds, linear (seam) welds, or any combination thereof. The combination of the mating interfaces with welding eliminates radiation leakage through the seam and ensures that the shielding does not rely solely on the weldment quality.

Figure 4:
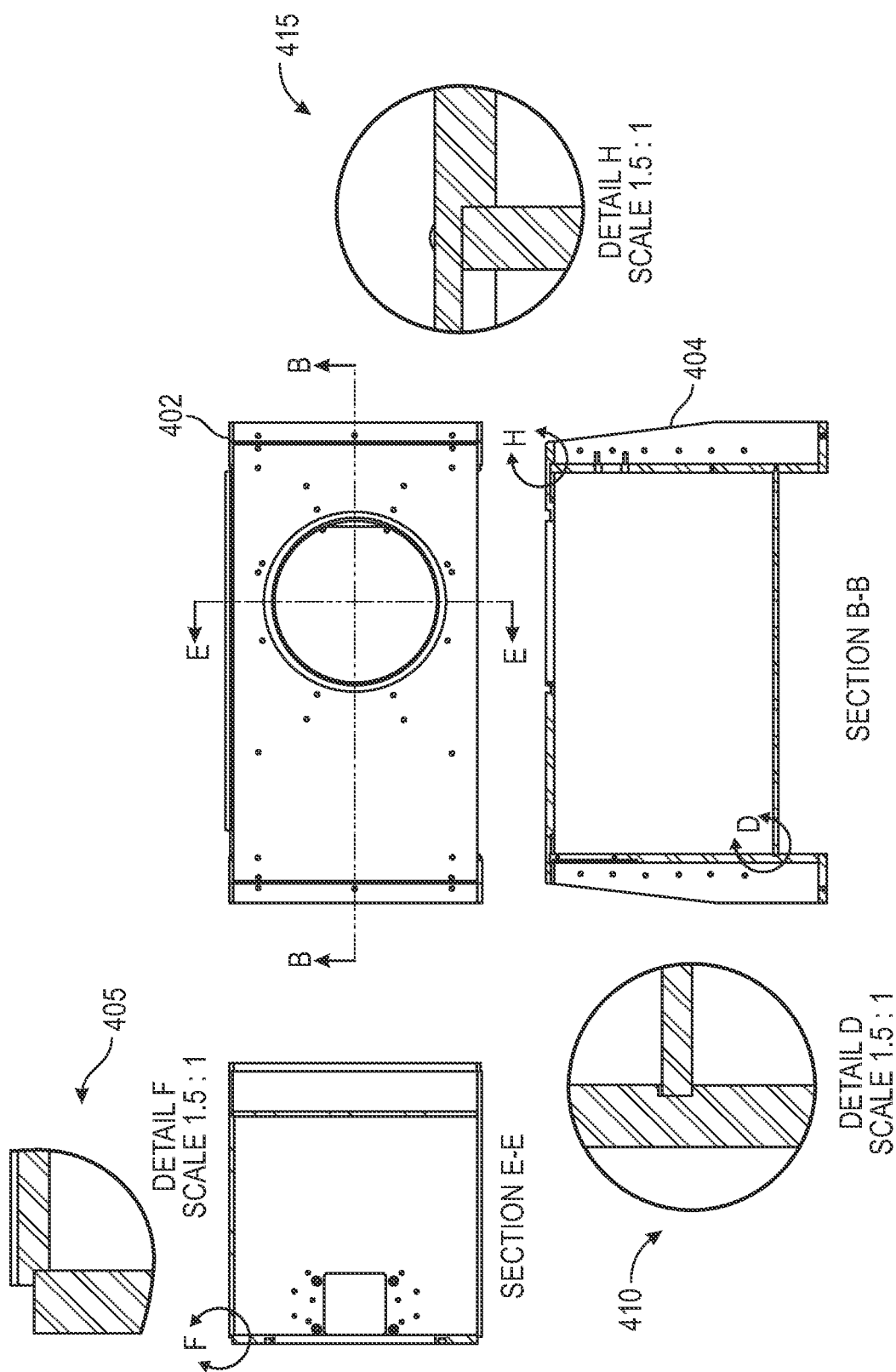
FIG. 4 shows several examples of joined panels for the shielding enclosure.

FIG. 4 shows several examples of joined panels for the x-ray shield enclosure 120 of some embodiments. A top-down view 402 and a side view 404 are shown in FIG. 4. Section E-E, taken along line E-E, illustrates a view facing from the front panel towards the back panel, with detail F showing (at a 1.5:1 scale) a joint 405 of the side panel with the top panel. In this example, the side panel has a groove into which the top panel fits along its length. Section B, taken along line B-B, illustrates a view from one side panel to the other side panel, with detail D showing (at a 1.5:1 scale) a joint 410 of the bottom panel with the back panel. In this example, the back panel has a groove to receive the bottom panel. Section B-B also shows (at a 1.5:1 scale) detail H of a joint 415 between the top panel with the front panel. In this example, the top panel has a groove into which the front panel fits along its length. In each case, the joints are stitch-welded to ensure that there is no gap between the joined panels, through which radiation may leak.

The x-ray shield enclosure 120 is intended to provide a substantially enclosed space once incorporated into a fully assembled system. For example, as described in some embodiments herein, there can be openings in the x-ray shield enclosure 120 allow the attachment of additional equipment to the x-ray shield enclosure 120, such as, but not limited to, an x-ray assembly 110 that can include any suitable combination of one or more x-ray sources, one or more collimators, etc. In such cases, a port in the x-ray shield enclosure 120 then obtains shielding from the x-ray assembly 110 attached to the x-ray shield enclosure 120 at the port. Similarly, there can be a port in the x-ray shield enclosure 120 for attaching the detector assembly 112 and allowing data to be transmitted out of the x-ray shield enclosure 120 during operation. Again, the detector assembly 112 can provide shielding to attenuate x-rays that may pass through the port utilized in this case as well. These are a couple of non-limiting examples. Other ports and other assemblies may be included in other embodiments.

Figure 5A:
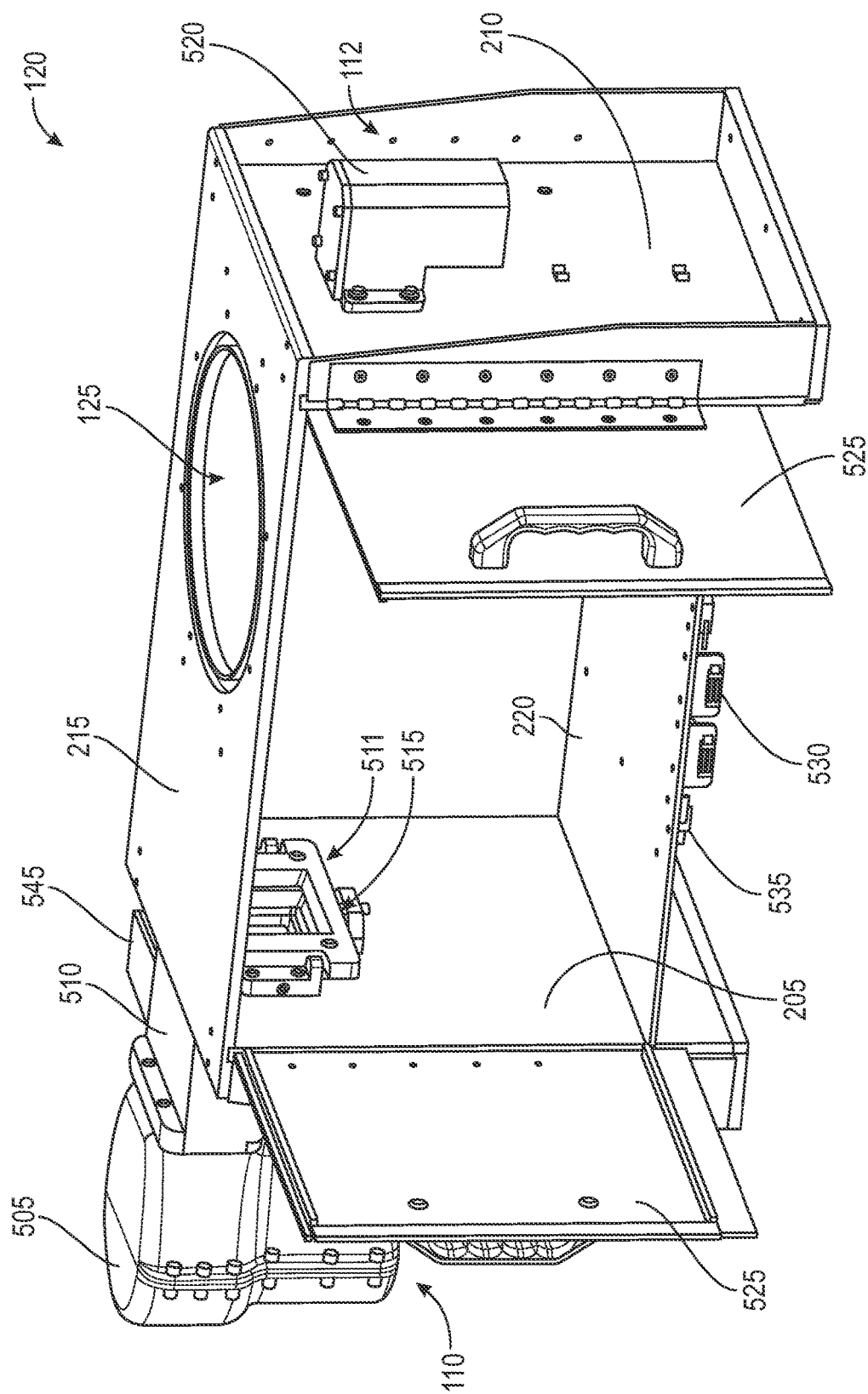
FIG. 5A shows a perspective view of the shield enclosure of some embodiments.

FIG. 5A shows a perspective view of the x-ray shield enclosure of some embodiments. In FIG. 5A, the components of the x-ray assembly 110 are visible, rigidly mounted to the back panel 205. The x-ray assembly 110 includes in some embodiments an x-ray tube 505, a primary collimator 510, and a secondary collimator 515. A cable feedthrough 520 for the detector assembly 112, rigidly mounted to the front panel 120, is also visible in this view. For example, in some embodiments the x-ray tube 505 provides 70 kV of voltage, 12 kW of power, and has a 0.3 mm focal spot. In some embodiments, as shown in an exploded view of the x-ray assembly 110 in FIG. 5B, the x-ray assembly 110 also includes a 0.2 mm thick copper (Cu) filter 517 that is sandwiched between the x-ray tube 505 and the primary collimator 510.

In this example, the x-ray tube 505 is directly mounted to the primary collimator 510, and the primary collimator 510 is directly attached to the outside of the back panel 205, around a port 511 in the back panel that permits the x-ray beam 114 (not shown in FIG. 5A) to emerge from the x-ray tube 505, be collimated by the primary collimator 510, and enter the enclosed space 122. The secondary collimator 515 may be mounted to the inside of the back panel 205, and the position may be adjustable (e.g., within ±2 mm) along the X-Y plane (parallel to the surface of the top panel 215) to ensure that the x-ray beam 114 falls upon the x-ray detector 115. As shown in FIG. 5C, the adjustment of the secondary collimator 515 may be controlled by a preload spring 518a, an X-collimator plate adjustment set screw 518b, and a Y-collimator plate adjustment set screw 518c.

Figure 5B:
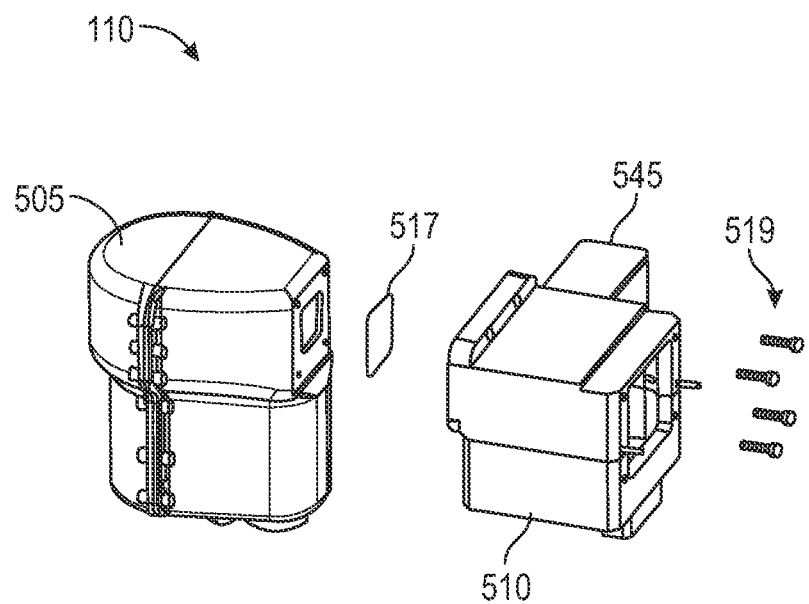
FIG. 5B shows the components of the x-ray assembly in some embodiments.
Figure 5C:
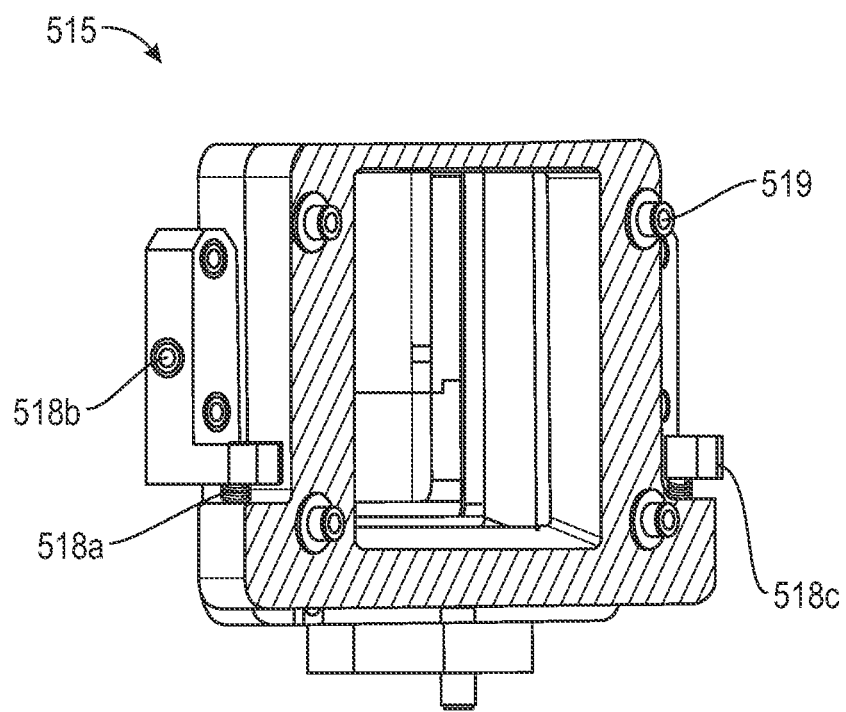
FIG. 5C shows a detail view of the secondary collimator in some embodiments.

The components of the x-ray assembly 110 are attached to each other using hardware fasteners, such as but not limited to mounting screws 519, as shown in FIG. 5B and FIG. 5C. The interfaces between the x-ray tube 505, the primary collimator 510, the back panel 205, and the secondary collimator 515 may be welded to prevent leakage of radiation.

Figure 5D:
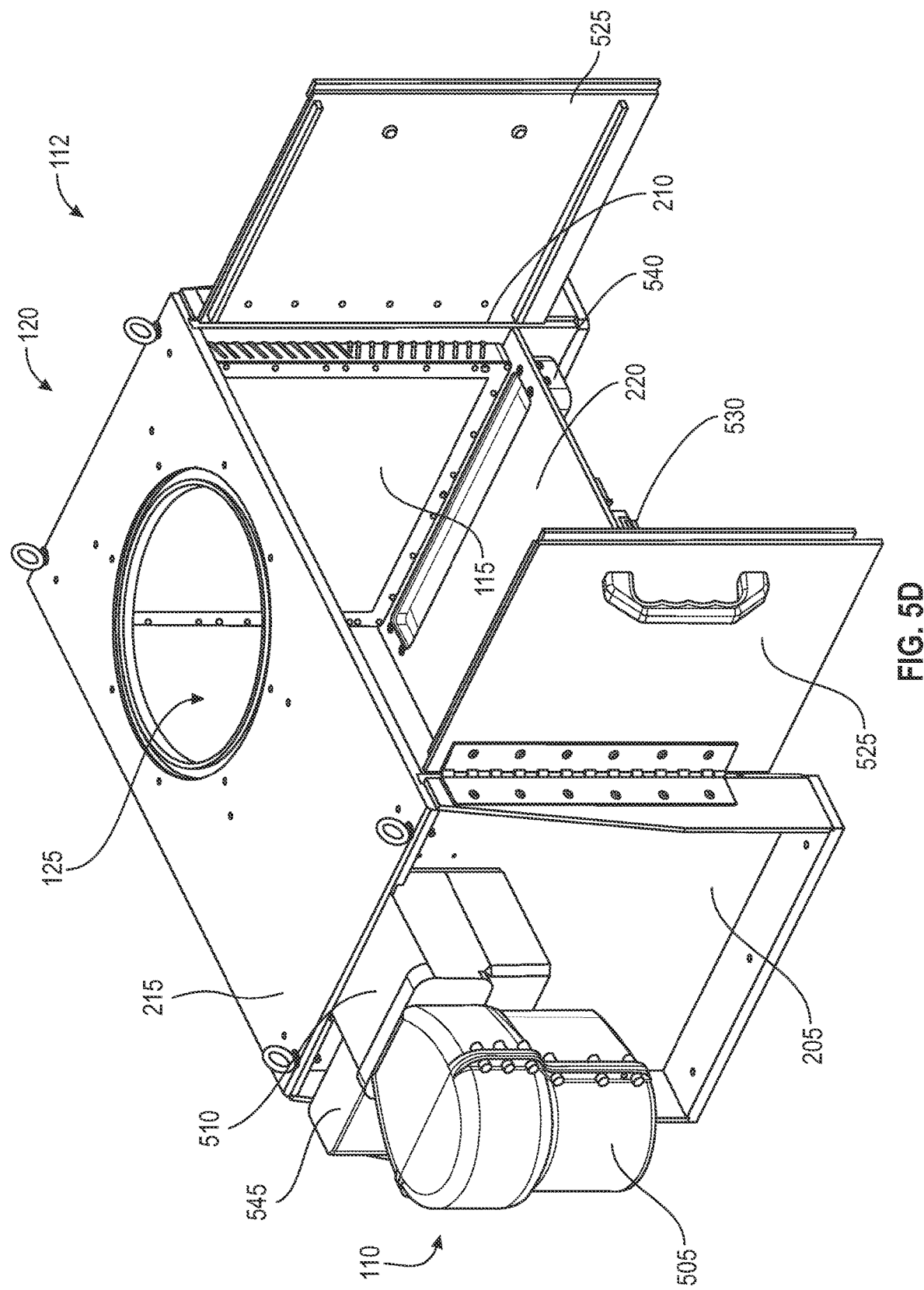
FIG. 5D shows the components of the detector assembly in some embodiments.

In FIG. 5D, the components of the detector assembly 112 are visible, rigidly mounted to the front panel 210. The detector assembly 112 includes in some embodiments the x-ray detector 115 that is mounted to the inside of the front panel 210, an anti-scatter grid (not shown in FIG. 5D). In some embodiments, the detector assembly includes a cable feedthrough 520 (shown in FIG. 5A) that is mounted to the outside of the front panel 210. Electronic signals from the x-ray detector 115 (inside the x-ray shield enclosure 120) are passed through cables in the cable feedthrough 520 to electronics and processors (outside the x-ray shield enclosure 120), for processing and analysis.

In some embodiments, the x-ray detector 115 is a flat panel detector. For example, a flat panel detector may provide 3052 pixels×3052 pixels resolution, 0.1 mm pixel pitch, and 40 frames-per-second (FPS) for 1×1 bins and 80 FPS for 2×2 bins. As an example, an anti-scatter grid may provide a 5:1 ratio, 10 lines/mm, and focal distance of 775 mm. However, the broad concepts of this invention are not limited to only those embodiments.

One or both of the primary collimator 510 and the secondary collimator 515 may be configured to collimate the x-ray beam 114 coverage on the x-ray detector 115. For example, in some embodiments, the collimators may collimate the beam so that the dimensions of the beam are 307.2 mm×307.2 mm, and extend 1 mm outside the active area of the x-ray detector 115 (dimensions 305.2 mm×305.2 mm). In some embodiments, the beam axis intersects the active plane of the x-ray detector 115, at a position 2 mm below the top active area edge of the x-ray detector 115. However, the broad concepts of this invention are not limited to only those embodiments.

Furthermore, access can be provided to the interior of the x-ray shield enclosure 120 by one or more access doors 525, in some embodiments. The one or more access doors 525 can be structured to interface with surrounding structures of the x-ray shield enclosure, and possibly with each other, so there are no gaps without, or with reduced, x-ray attenuating material. Some embodiments of such structures are described in more detail herein. However, the broad concepts of this invention are not limited to only those embodiments.

Figure 5E:
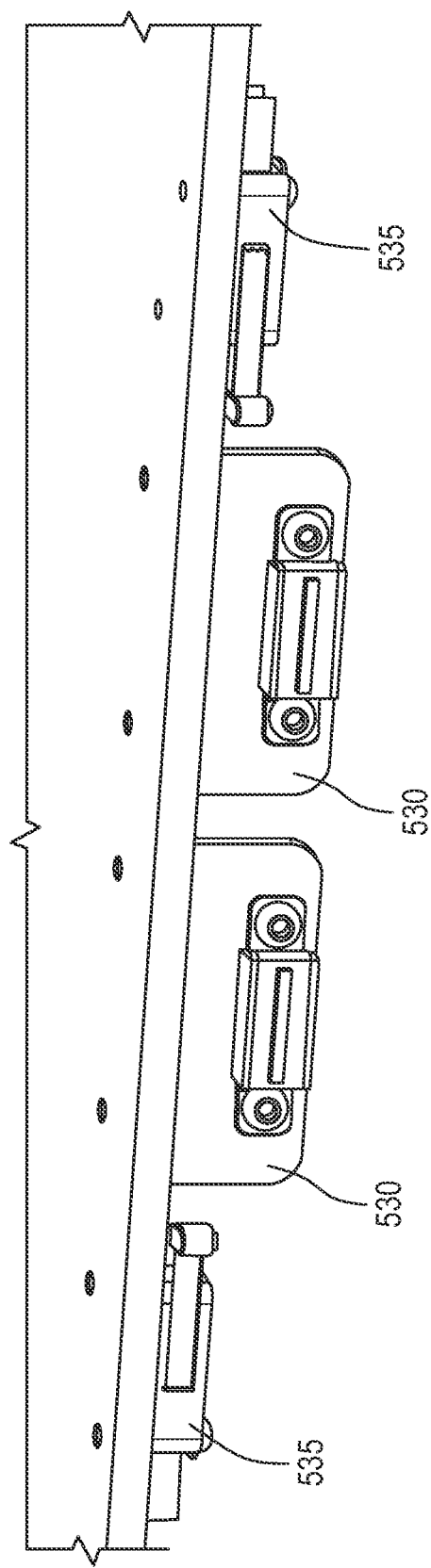
FIG. 5E shows access doors to the shielding enclosure in some embodiments that are secured by magnetic door latches when closed, and which engage safety switches that are used as an x-ray radiation hardware interlock.

In some embodiments, as shown in FIG. 5D and FIG. 5E, the access doors 525 are secured by magnetic door latches 530 when closed. In addition, in the closed and secured position, the access doors 525 engage safety switches 535 that are used as an x-ray radiation hardware interlock. For example, the safety switches 535 may be single-pole double-throw (SPDT) switches. Both of the safety switches 535 must be engaged for operation of the x-ray assembly 110. This redundant design ensures that the x-ray tube 505 is prevented from generating the x-ray beam 114 while at least one of the access doors 525 are open. A light fixture 540 also illuminates the interior of the x-ray shield enclosure 120 when the access doors 525 are open.

Figure 6:
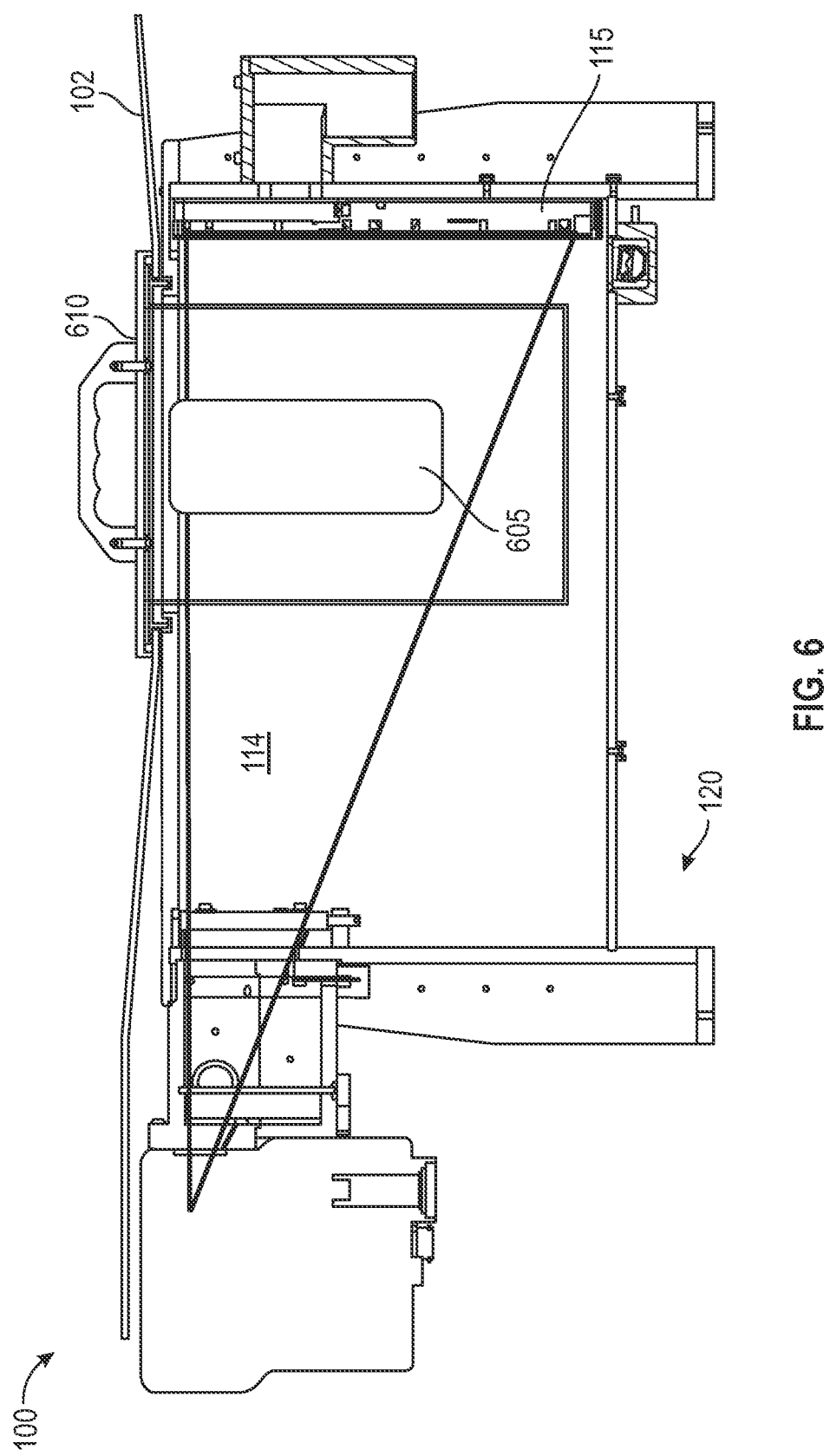
FIG. 6 conceptually illustrates inserting a breast phantom into the FOV of the x-ray beam.

In some embodiments, the system 100 can be configured for phantom imaging instead of a patient's breast. This is useful, for example, during system calibration, dose measurement, and other types of maintenance and testing. FIG. 6 conceptually illustrates inserting a breast phantom 605 into the FOV of the x-ray beam 114 from above, through the opening 105 in the table 102 and the aperture 125 in the x-ray shield enclosure 120. Since there is no patient in this scenario, in some embodiments a shielding lid 610 is inserted onto the patient table 102 during operation, to prevent radiation leakage through the opening 105.

Figure 7:
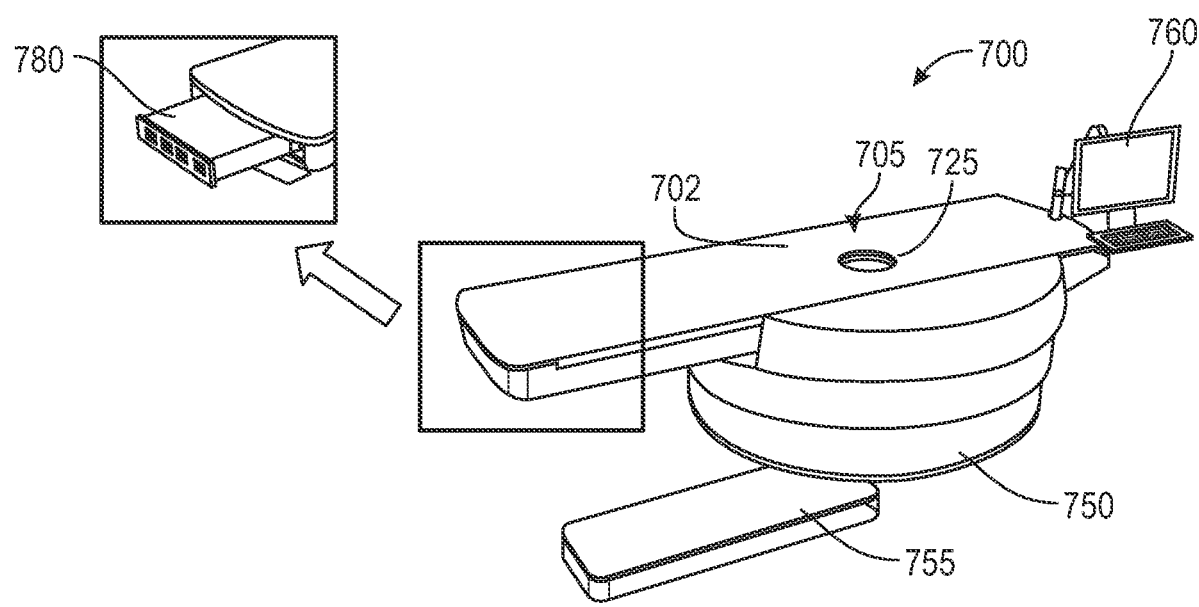
FIG. 7 shows another embodiment of a self-shielded breast CT system, which includes an operator workstation.

FIG. 7 shows another embodiment of a self-shielded breast CT system 700. The system 700 is similar to the embodiment of the system 100 discussed above with respect to FIG. 1, and like reference numerals have been used to refer to the same or similar components. A detailed description of these components will be omitted, and the following discussion focuses on the differences between these embodiments. Any of the various features discussed with any one of the embodiments discussed herein may also apply to and be used with any other embodiments.

FIG. 7 shows an external view of the system 700, with a patient table 702 having an opening 705 for the patient's breast. A ring interface 725 is also visible to permit rotational motion of the patient table 702 relative to the x-ray shield enclosure (not visible in FIG. 7). The x-ray shield enclosure and rotating platform are hidden by a cowling 750 that protects the mechanical components, as well as the operator and patient. Electronics and mechanical components associated with the drive assembly, including a motor to rotate the platform and a lift to raise and lower the patient bed, are also protected by a secondary cowling 755.

FIG. 7 also shows that the system 700 includes a workstation 760. The workstation 760 includes a user interface for a user to control the system 700, such as a keyboard and mouse, and a display. In some embodiments the display is also a touchscreen interface for control and operation of the system 700, e.g., for control and operation of the x-ray assembly 110 and the gantry assembly 305.

In some embodiments, the system 700 includes a data processor 780 that is communicatively coupled to the detector assembly 112, and configured to generate, based on signals received from the detector assembly 112 in response to receiving the x-ray beam 114, an x-ray image and/or a computed tomography image of the breast. The data processor may also be communicatively coupled to other systems, such as a picture archiving and communication system (PACS) (not shown in FIG. 7), and/or the workstation 760 so that the image of the breast may be displayed for the user to review. In some embodiments, the data processor 780 is a rack-mounted computer that is mounted underneath the patient table 702.

Figure 8:
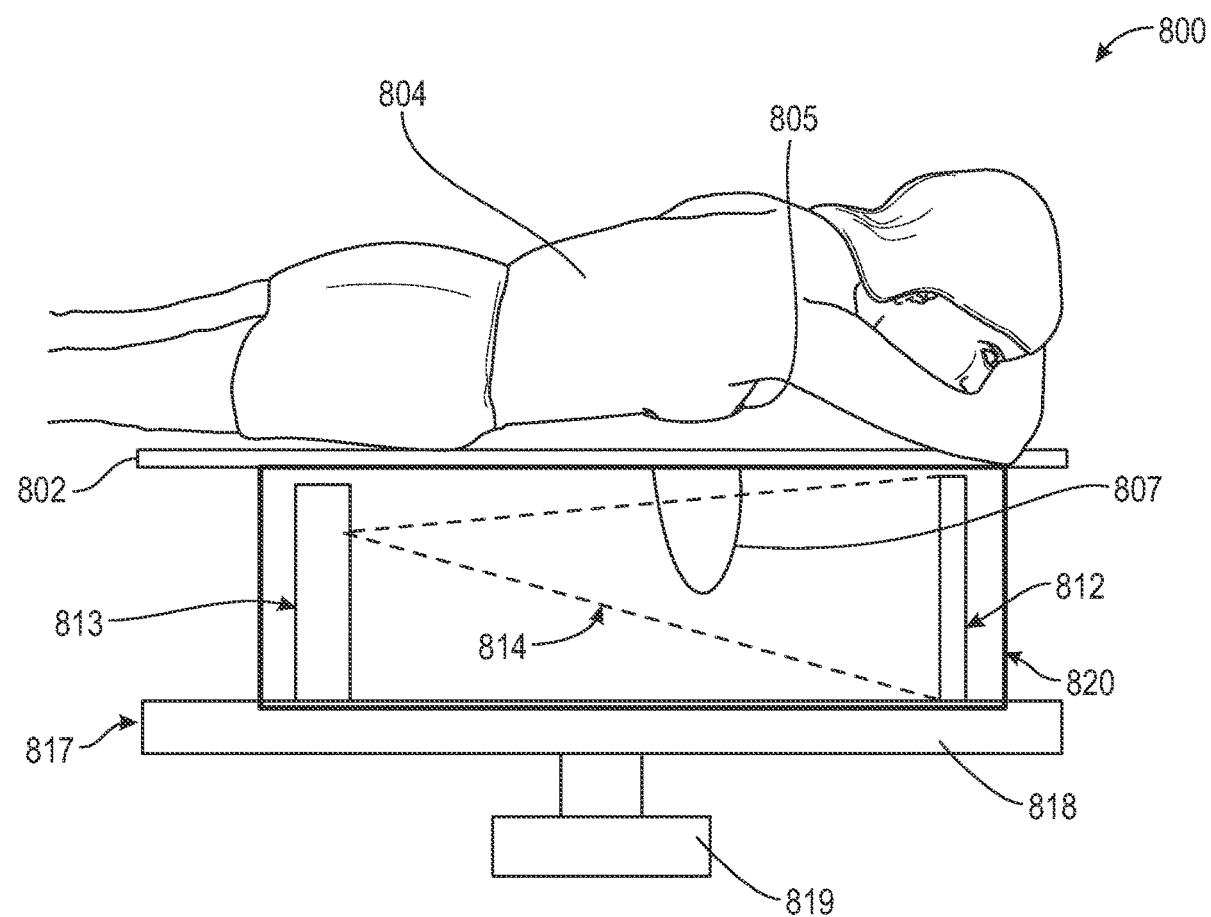
FIG. 8 shows another example of a self-shielded CT system of some embodiments, in which both the x-ray source and the x-ray detector are mounted to the platform inside the shield enclosure.

FIG. 8 shows another example of a self-shielded CT system 800 of some embodiments. The system 800 is similar to the embodiment of the system 100 discussed above with respect to FIG. 1, and like reference numerals have been used to refer to the same or similar components. A detailed description of these components will be omitted, and the following discussion focuses on the differences between these embodiments. Any of the various features discussed with any one of the embodiments discussed herein may also apply to and be used with any other embodiments.

In this example, the self-shielded CT system 800 is a system for breast computed tomography (CT). The system includes a table 802 configured to support a patient 804 in a prone position, and has an opening 805 that is positioned so that the patient's breast 807 extends downwards through the opening 805 into the imaging field of view (FOV).

A gantry assembly 817 is positioned beneath the table 802, and includes a platform 818 that is driven to rotate by a motor 819. The system 800 includes a x-ray shielding enclosure 820, an x-ray tube 813, and an x-ray detector 812. In this example, the x-ray detector 812 and the x-ray tube 813 are both coupled to the platform 818 to rotate around the breast, with the x-ray tube 813 positioned to irradiate at least a portion of the breast 807 with an x-ray beam 814, and the x-ray detector 812 positioned to receive the x-ray beam 814 after irradiating the breast 807.

The shielding enclosure 820 is rigidly mounted atop the platform 818 and also rotates along with it and the x-ray tube 813, and the x-ray detector 812. In this embodiment, the shielding enclosure 820 fully encloses the x-ray tube 813 and the x-ray detector 812.

The terms "light" and "optical" are intended to have broad meanings that can include both visible regions of the electromagnetic spectrum as well as other regions, such as, but not limited to, infrared and ultraviolet light and optical imaging, for example, of such light.

The terms "computer", "server", "processor", and "memory" all refer to electronic or other technological devices. These terms exclude people or groups of people. As used in this specification, the terms "computer readable medium," "computer readable media," and "machine readable medium," etc. are entirely restricted to tangible, physical objects that store information in a form that is readable by a computer. These terms exclude any wireless signals, wired download signals, and any other ephemeral signals.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but not limited to) a hard disk drive and/or a removable storage drive, representing a floppy diskette drive, a magnetic tape drive, an optical disk drive, a read-only compact disk (CD-ROM), digital versatile discs (DVDs), flash memory (e.g., SD cards, mini-SD cards, micro-SD cards, etc.), read-only and recordable Blu-Ray® discs, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

Some embodiments include electronic components, such as microprocessors, storage and memory that store computer program instructions in a machine-readable or computer-readable medium (alternatively referred to as computer-readable storage media, machine-readable media, or machine-readable storage media). The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The computer may also include an input device may include any mechanism or combination of mechanisms that may permit information to be input into the computer system from, e.g., a user. The input device may include logic configured to receive information for the computer system from, e.g., a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or another camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions, including application-specific integrated circuits (ASICs) and field-programmable gate arrays (FPGAs). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

The term "network" is intended to include any communication network, including a local area network ("LAN"), a wide area network ("WAN"), an Intranet, or a network of networks, such as the Internet.

The term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the spirit or scope of the disclosure, as appreciated by those skilled in the art in light of the above teachings. It is therefore to be understood that, within the scope of the claims and their equivalents, the invention may be practiced otherwise than as specifically described. Moreover, features described in connection with one embodiment may be used in conjunction with other embodiments, even if not explicitly stated above.

We claim:

1. A system for at least one of breast examinations and procedures, comprising:
   a table configured to support a patient in a prone position, the table defining an opening that is positioned for a breast of the patient to extend downwards therethrough;
   a gantry assembly positioned beneath the table, said gantry assembly comprising a platform and a drive assembly configured to rotate said platform relative to said table;
   an x-ray shield enclosure attached to said platform of said gantry so as to be rotatable along with said platform, said x-ray shield enclosure defining a substantially enclosed space therein and further defining an opening through a side thereof that is aligned with said opening defined by said table for said breast of said patient to extend downwards therethrough at least partially into said space defined by said x-ray shield enclosure;
   an x-ray assembly attached to the x-ray shield enclosure so as to be rotatable therewith, said x-ray assembly comprising an x-ray source positioned to irradiate with an x-ray beam at least a portion of the breast during operation; and
   a detector assembly attached to the x-ray shield enclosure to be rotatable therewith, the detector assembly comprising an x-ray detector positioned to receive at least a portion of the x-ray beam after passing through the breast,
   wherein the x-ray shield enclosure attenuates x-rays from said x-ray source sufficiently for users of said system to be in a vicinity of said x-ray shield enclosure during operation of said system without further shielding while complying with radiation safety.

2. The system of claim 1, wherein said x-ray shield enclosure comprises low carbon steel.

3. The system of claim 1, wherein said x-ray shield enclosure consists essentially of low carbon steel.

4. The system of claim 1, wherein said x-ray shield enclosure comprises at least one of lead, tungsten, steel, or other high-Z radiation shielding material.

5. The system of claim 1, wherein said x-ray shield enclosure is substantially a polygonal box in which at least two adjacent panels are separated by one of a bend in an integral sheet of material or joined so as to minimize x-ray leakage along a seam between said at least two adjacent panels of material.

6. The system of claim 5, wherein said polygonal box comprises seams between adjacent panels that are joined by tongue and groove interfaces that are welded together.

7. The system of claim 1, further comprising a ring interface attached to said table and rotatably connected to said x-ray shield enclosure so as to allow relative rotation between of said x-ray shield enclosure and said table,
   wherein said ring interface and said x-ray shield enclosure interconnect without leaving gaps for unattenuated x-rays to pass therethrough.

8. The system of claim 1, further comprising a data processor communicatively coupled to the detector and configured to generate, based on a plurality of signals received from the detector in response to receiving the x-ray beam, a computed tomography image of the breast.

9. The system of claim 1, further comprising a safety shield rigidly mounted to the patient table thereunder and extending downward into said substantially enclosed space of said x-ray shield enclosure so that the safety shield remains static during rotation of the platform,
   wherein the safety shield is substantially transparent to the x-ray beam and light.

10. The system of claim 1, wherein the x-ray detector is a flat-panel detector,
    wherein the x-ray beam is a cone beam, and
    wherein the system is configured to perform cone-beam computed tomography.

11. An x-ray shield enclosure for a system for at least one of breast examinations and procedures, comprising:
    x-ray attenuating material forming a substantially enclosing box defining a substantially enclosed space therein,
    wherein a side of said substantially enclosing box defines an opening therethrough that is suitable to be aligned with an opening defined by a table of said system such that a breast of a patient can extend downwards through said opening of said x-ray shield enclosure at least partially into said space defined by said x-ray shield enclosure,
    wherein said x-ray shield enclosure is further configured to be attached to a rotatable platform of a gantry of said system so as to be rotatable along with said platform, and
    wherein the x-ray shield enclosure attenuates x-rays from an x-ray source sufficiently for users of said system to be in a vicinity of said x-ray shield enclosure during operation of said system without further shielding while complying with radiation safety.

12. The x-ray shield enclosure of claim 11, wherein said x-ray shield enclosure comprises low carbon steel.

13. The x-ray shield enclosure of claim 11, wherein said x-ray shield enclosure consists essentially of low carbon steel.

14. The x-ray shield enclosure of claim 11, wherein said x-ray shield enclosure comprises at least one of one of lead, tungsten, steel, or other high-Z radiation shielding material.

15. The x-ray shield enclosure of claim 11, wherein said enclosing box comprises at least two adjacent panels that are separated by one of a bend in an integral sheet of material or joined so as to minimize x-ray leakage along a seam between said at least two adjacent panels of material.

16. The x-ray shield enclosure of claim 15, wherein said enclosing box comprises seams between adjacent panels that are joined by tongue and groove interfaces that are welded together.

17. A method of manufacturing a system for at least one of breast examinations and procedures, comprising:
    providing a table configured to support a patient in a prone position, the table defining an opening that is positioned for a breast of the patient to extend downwards therethrough;
    providing a gantry assembly positioned beneath the table, said gantry assembly comprising a platform and a drive assembly configured to rotate said platform relative to said table;
    attaching an x-ray shield enclosure to said platform of said gantry so as to be rotatable along with said platform, said x-ray shield enclosure defining a substantially enclosed space therein and further defining an opening through a side thereof that is aligned with said opening defined by said table for said breast of said patient to extend downwards therethrough at least partially into said space defined by said x-ray shield enclosure;

attaching an x-ray assembly to the x-ray shield enclosure so as to be rotatable therewith, said x-ray assembly comprising an x-ray source positioned to irradiate with an x-ray beam at least a portion of the breast during operation; and attaching a detector assembly to the x-ray shield enclosure to be rotatable therewith, the detector assembly comprising an x-ray detector positioned to receive at least a portion of the x-ray beam after passing through the breast, wherein the x-ray shield enclosure attenuates x-rays from said x-ray source sufficiently for users of said system to be in a vicinity of said x-ray shield enclosure during operation of said system without further shielding while complying with radiation safety.

18. The method of claim 17, wherein said x-ray shield enclosure comprises low carbon steel.

19. The method of claim 17, wherein said x-ray shield enclosure consists essentially of low carbon steel.

20. The method of claim 17, wherein said x-ray shield enclosure comprises at least one of lead, tungsten, steel, or other high-Z radiation shielding material.

21. The method of claim 17, further comprising:
rigidly attaching a ring interface to said table; and
rotatably attaching said x-ray shield enclosure connected to said ring interface so as to allow relative rotation between of said x-ray shield enclosure and said table, wherein said ring interface and said x-ray shield enclosure interconnect without leaving gaps for unattenuated x-rays to pass therethrough.

22. A method of producing an x-ray shield enclosure for a system for at least one of breast examinations and procedures, comprising:

forming a substantially enclosing box from x-ray attenuating material so as to define a substantially enclosed space therein; and forming an opening through a side of said substantially enclosing box, said opening being suitable to be aligned with an opening defined by a table of said system such that a breast of a patient can extend downwards through said opening of said x-ray shield enclosure at least partially into said space defined by said x-ray shield enclosure, wherein said x-ray shield enclosure is further configured to be attached to a rotatable platform of a gantry of said system so as to be rotatable along with said platform, and wherein the x-ray shield enclosure attenuates x-rays from an x-ray source sufficiently for users of said system to be in a vicinity of said x-ray shield enclosure during operation of said system without further shielding while complying with radiation safety.

23. The method of claim 22, wherein said forming said substantially enclosing box comprises attaching a plurality of panels of said x-ray attenuating material at seams between adjacent panels that are joined by tongue and groove interfaces that are welded together.

* * * * *